(12) United States Patent
Cramail et al.

(10) Patent No.: US 9,926,288 B2
(45) Date of Patent: Mar. 27, 2018

(54) FIVE-MEMBERED CYCLIC BISCARBONATES BEARING AMIDE LINKAGES, THEIR PREPARATION AND THEIR USES FOR THE PREPARATION OF POLYMERS

(71) Applicants: UNIVERSITÉ DE BORDEAUX, Bordeaux (FR); INSTITUT POLYTECHNIQUE DE BORDEAUX, Talence (FR); Centre National de la Recherche Scientifique, Paris (FR); INSTITUT DES CORPS GRAS ETUDES ET RECHERCHES TECHNIQUES—ITERG, Pessac (FR)

(72) Inventors: Henri Cramail, Sainte Terre (FR); Etienne Grau, Talence (FR); Carine Alfos, Pessac (FR); Lise Maisonneuve, Talence (FR)

(73) Assignees: UNIVERSITÉ DE BORDEAUX, Bordeaux (FR); INSTITUT POLYTECHNIQUE DE BORDEAUX, Talence (FR); CENTRE NATIONAL DE LA RECHERCHE SCIENTIFIQUE (C.N.R.S), Paris (FR); INSTITUT DES CORPS GRAS ETUDES ET RECHERCHES TECHNIQUES—ITERG, Pessac (FR)

( * ) Notice: Subject to any disclaimer, the term of this patent is extended or adjusted under 35 U.S.C. 154(b) by 0 days.

(21) Appl. No.: 15/104,956

(22) PCT Filed: Dec. 16, 2014

(86) PCT No.: PCT/EP2014/077977
§ 371 (c)(1),
(2) Date: Jun. 15, 2016

(87) PCT Pub. No.: WO2015/091494
PCT Pub. Date: Jun. 25, 2015

(65) Prior Publication Data
US 2016/0326132 A1 Nov. 10, 2016

(30) Foreign Application Priority Data
Dec. 16, 2013 (EP) .................................... 13306736

(51) Int. Cl.
*C07D 317/38* (2006.01)
*C07D 303/46* (2006.01)
(Continued)

(52) U.S. Cl.
CPC ......... *C07D 317/38* (2013.01); *C07D 303/46* (2013.01); *C08G 71/04* (2013.01); *C08K 5/20* (2013.01)

(58) Field of Classification Search
CPC .................................................. C07D 317/38
(Continued)

(56) References Cited

U.S. PATENT DOCUMENTS 2,975,149 A  3/1961 Port
3,235,568 A  2/1966 Findley
(Continued)

FOREIGN PATENT DOCUMENTS

DE  4218837 A1  12/1993
EP  13306736  6/2015
(Continued)

OTHER PUBLICATIONS

Aurelie, et al., Solubility in $CO_2$ and carbonation studies of epoxidized fatty acid diesters: towards novel precursors for polyurethane synthesis, Green Chem., 12, p. 2205-2213, 2010.
EPO Search Report re Application No. 13306736.3, dated Mar. 24, 2014.
Gelb, et al.; Epoxy resins from fats. Effect of structure of epoxystearamides on the physical properties of their phthalic anhydride cured resins, XP002720278, Chemical Abstract Service, Database Accession No. 1962:423856.
International Search Report re Application No. PCT/EP2014/077977, dated Feb. 19, 2015.
RN 1005042-91-0; XP002720279, Chemical Abstract Service, Database Accession No. 1005042-91-0; Feb. 22, 2008.

*Primary Examiner* — Duc Truong
(74) *Attorney, Agent, or Firm* — Knobbe, Martens, Olson & Bear, LLP

(57) ABSTRACT

A compound is of formula (I):

in which $A_1$ and $A_1'$ are independently from each other a linear or branched alkylene radical including from 1 to 20 carbon atom(s); $A_2$ is in particular a linear or branched alkylene radical including from 1 to 200 carbon atom(s); $A_3$ is H or a linear or branched alkyl radical including from 1 to 15 carbon atom(s) and $R_1$ and $R_1'$ are independently from each other H or a linear or branched alkyl radical comprising from 1 to 20 carbon atom(s). The compounds of formula (I) can be used in particular for the preparation of poly(hydroxyurethane)s and epoxy resins.

14 Claims, No Drawings

(51) Int. Cl.
*C08K 5/20* (2006.01)
*C08G 71/04* (2006.01)

(58) Field of Classification Search
USPC .......................................................... 528/346
See application file for complete search history.

(56) References Cited

U.S. PATENT DOCUMENTS

| | | |
|---|---|---|
| 3,873,457 A | 3/1975 | Magne |
| 2008/0089924 A1 | 4/2008 | Nojima |

FOREIGN PATENT DOCUMENTS

| | | |
|---|---|---|
| WO | WO 2003/031424 A1 | 4/2003 |
| WO | WO 2013/060950 A1 | 5/2013 |
| WO | WO 2013/092011 A1 | 6/2013 |
| WO | WO 2015/091494 A1 | 6/2015 |

FIVE-MEMBERED CYCLIC BISCARBONATES BEARING AMIDE LINKAGES, THEIR PREPARATION AND THEIR USES FOR THE PREPARATION OF POLYMERS

This application is the U.S. National Phase under 35 U.S.C. § 371 of International Application No. PCT/EP2014/077977, filed Dec. 16, 2014, designating the U.S., and published in English as WO 2015/091494 on Jun. 25, 2015, which claims priority to European Patent Application No. EP 13306736.3, filed Dec. 16, 2013.

BACKGROUND OF THE INVENTION

Field of the Invention

The present invention concerns new 5-membered cyclic biscarbonates, their preparation and their uses, in particular for the preparation of polymers such as poly(hydroxyurethane)s (PHUs) and epoxy resins.

Description of Related Art

Polyurethanes (PUs) are produced using (poly)isocyanates. Isocyanates are toxic compounds, manufactured from an amine and phosgene which is also highly toxic when inhaled. The industrial process for the preparation of isocyanates comprises the reaction of an amine with an excess of phosgene leading to isocyanate and a mixture of phosgene and hydrogen chloride.

Therefore, finding alternative routes for the synthesis of PUs which avoid the use of isocyanates is of high importance.

Several ways are known to produce more sustainable non isocyanate polyurethanes from non-toxic vegetable oil derivatives, such as:

(i) the ring-opening of cyclic carbonates bearing ester groups by amines, (ii) the transurethane process, and (iii) the self-condensation method based on the Curtius rearrangement in which the AB-type monomer contains both hydroxyl and acyl azide groups.

Therefore, there is a need to develop these ways of producing non isocyanate polyurethanes, using non-toxic and renewable reactants.

BRIEF SUMMARY OF THE INVENTION

The aim of the present invention is to provide new cyclic carbonates, useful for the preparation of polymers such as PHUs, which derive from non-toxic and renewable vegetable oil derivatives.

Thus, the invention relates to a compound of formula (I):

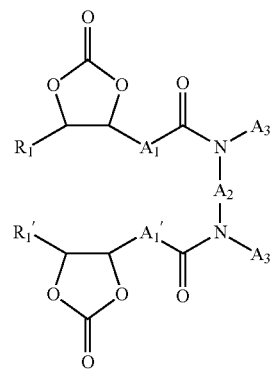

wherein:
$A_1$ and $A_1'$ are independently from each other a linear or branched alkylene radical comprising from 1 to 20 carbon atom(s);

$A_2$ is chosen from the group consisting of:
  a linear or branched alkylene radical comprising from 1 to 200 carbon atom(s), one or more carbon atom(s) being optionally replaced by an oxygen atom;
  an arylene radical comprising from 6 to 14 carbon atoms, optionally functionalized in ortho, meta or para, with a linear or branched alkyl radical comprising from 1 to 10 carbon atom(s), one or more carbon atom(s) being optionally replaced by an oxygen atom;
  a radical of formula —$B_1$—$B_2$— wherein:
    $B_1$ is a cycloalkylene comprising from 3 to 15 carbon atoms, in which one or more carbon atom(s) is optionally substituted by at least one linear or branched alkyl group comprising from 1 to 15 carbon atom(s), and
    $B_2$ is a linear or branched alkylene radical comprising from 1 to 15 carbon atom(s);

$A_3$ is H or a linear or branched alkyl radical comprising from 1 to 15 carbon atom(s);
or wherein $A_2$ and $A_3$, together with the two nitrogen atoms bearing them, may form a saturated heterocyclyl group comprising from 3 to 8 members; and
$R_1$ and $R_1'$ are independently from each other H or a linear or branched alkyl radical comprising from 1 to 20 carbon atom(s).

The vegetable oil-based poly- or biscyclic carbonates are usually bearing ester groups due to the inherent structure of the triglycerides. Surprisingly, the present inventors find that 5-membered biscarbonates bearing amide linkages can lead to PHUs. The present inventors thus synthesized PHUs without employing neither toxic and unstable diisocyanates, nor phosgene.

Definitions

In the context of the present invention, the term "alkyl" means a saturated aliphatic hydrocarbon group which may be linear or branched. "Branched" means that one or lower alkyl groups such as methyl, ethyl or propyl are attached to a linear alkyl chain. Alkyl groups comprise from 1 to 20 carbon atom(s). Preferred alkyl groups comprise 1, 2, 3, 4, 5, 6, 7, 8, 9 or 10 carbon atom(s).

The term "alkylene" means a saturated aliphatic hydrocarbon divalent radical which may be linear or branched. Preferred alkylene groups may have 3, 4, 5, 6, 7, 8, 9 or 10 carbon atoms.

By "cycloalkylene" is meant a cyclic, saturated hydrocarbon divalent group having 3 to 15 carbon atoms, in particular cyclopropyl or cyclohexyl groups.

The term "arylene" refers to an aromatic monocyclic, bicyclic or tricyclic hydrocarbon ring system comprising from 6 to 14 carbon atoms wherein any ring atom capable of substitution may be substituted by a substituent. A preferred arylene group is phenylene.

The term "heterocyclyl" refers to a saturated monocyclic, bicyclic or tricyclic hydrocarbon ring system, wherein any ring atom capable of substitution may be substituted by a substituent and wherein one or more carbon atom(s) are replaced by one or more heteroatom(s) such as nitrogen atom(s), oxygen atom(s) and sulfur atom(s); for example 1 or 2 nitrogen atom(s), 1 or 2 oxygen atom(s), 1 or 2 sulfur atom(s) or a combination of different heteroatoms.

In one embodiment, the heteroatoms of the heterocyclyl group are only the two nitrogen atoms of the amide linkages of the compound of formulae (I), (II) or (III). For example, the formed heterocyclyl is a piperazine group.

The term "halogen" refers to the atoms of the group 17 of the periodic table and includes in particular fluorine, chlorine, bromine, and iodine atoms.

Biscarbonates of Formula (I)

In one embodiment, $A_1$ and $A_1'$ comprise independently from each other from 1 to 12 carbon atom(s). More particularly, $A_1$ and $A_1'$ are independently chosen among linear alkylene radicals comprising 1 to 12 carbon atom(s). In a preferred embodiment, $A_1$ and $A_1'$ are chosen from linear alkylene radicals comprising between 6 and 12 carbon atoms, more preferably 8 carbon atoms. In one embodiment $A_1$ and $A_1'$ are identical.

In one embodiment, $A_2$ is a linear or branched alkylene radical comprising from 1 to 10 carbon atom(s). More particularly, $A_2$ is a linear alkylene radical comprising from 1 to 10 carbon atom(s). For example, $A_2$ comprises 3, 4 or 10 carbon atoms.

In one embodiment, $A_3$ is H or a linear or branched alkyl radical comprising from 1 to 10 carbon atom(s). In another embodiment, $A_3$ is chosen among H, a linear alkyl radical comprising from 1 to 6 carbon atoms or $A_2$ and $A_3$, together with the two nitrogen atoms bearing them form a saturated cyclic ring comprising 6 members.

In one embodiment, $A_2$ and $A_3$, together with the two nitrogen atoms bearing them, form a saturated heterocyclyl group comprising from 5 to 8 members, more particularly, form a saturated heterocyclyl group comprising 6 members, such as a piperazine group.

In one embodiment, $R_1$ and $R_1'$ are H. In another embodiment, $R_1$ and $R_1'$ are H and $A_1$ and $A_1'$ are both a linear alkylene radical comprising 8 carbon atoms.

In a particular embodiment, $A_1$ and $A_1'$ are identical and/or $R_1$ and $R_1'$ are identical.

In one embodiment, the compounds of formula (I) have the following formula (I'):

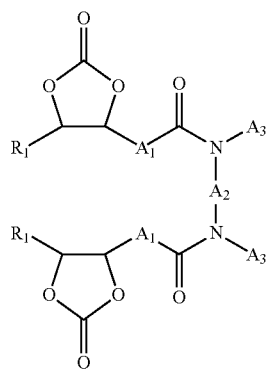

(I')

wherein $A_1$, $R_1$, $A_2$ and $A_3$ are as defined above.

The present invention relates to the following specific compounds:

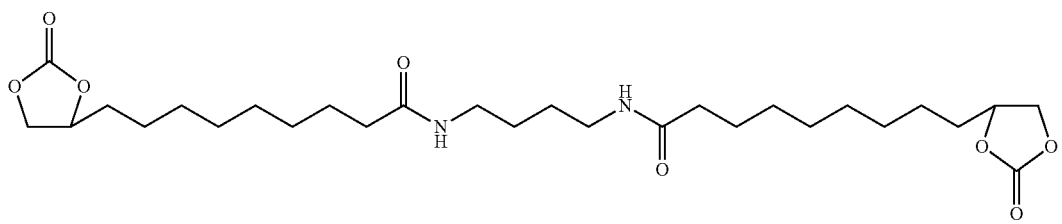

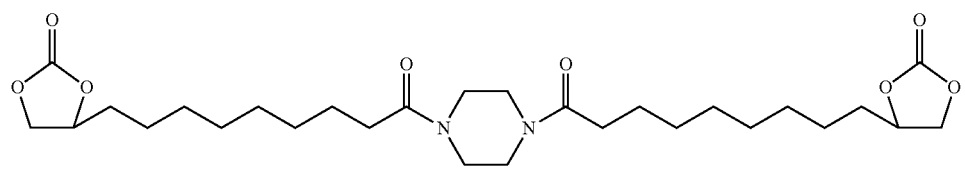

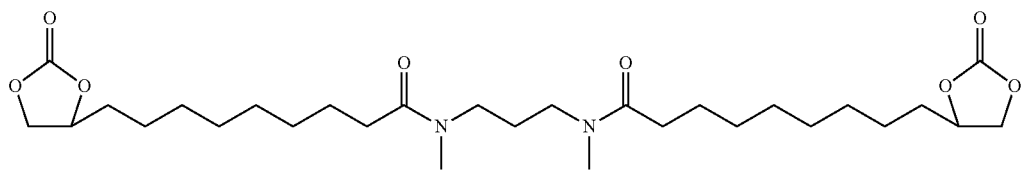

-continued

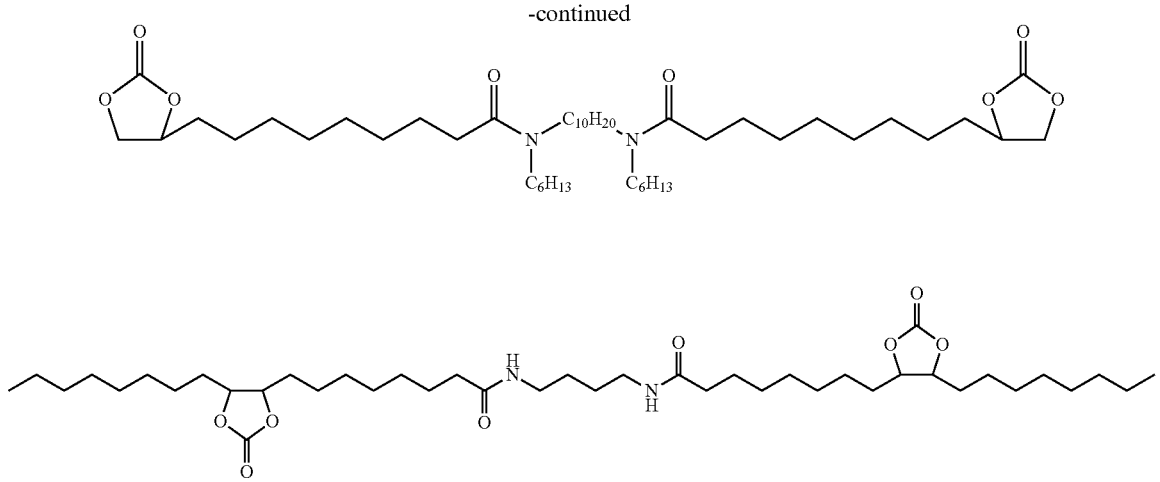

DETAILED DESCRIPTION OF THE INVENTION

Process of Preparation of the Biscarbonates of Formula (I)

The present invention also relates to a process of preparation of the compounds of formula (I) as defined above.

An advantage of the process of preparation of said biscarbonates is that it needs co-reactants, such as 1,4-diaminobutane, which can be issued from bio-based raw materials such as glutamic acid.

In one embodiment, the process for preparing a compound of formula (I) as defined above, comprises a carbonation step of a compound having formula (II):

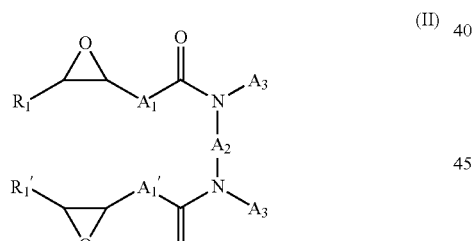

wherein $A_1$, $A_1'$, $A_2$, $A_3$, $R_1$ and $R_1'$ are as defined above.

In a particular embodiment, the carbonation step is carried out in the presence of $CO_2$ and a catalyst. Said catalyst may be chosen from the group consisting of tetrabutylammonium bromide (TBABr) or an imidazolium salt. In a particular embodiment, the catalyst is chosen among TBABr, 1-methyl-3-methylimidazolium iodide salt and 1,5,7-triazabicyclo[4.4.0]dec-5-enium bromide (TBDHBr). The catalyst may be in particular tetrabutylammonium bromide (TBABr).

In one embodiment, the carbonation step is carried out in the presence of $CO_2$ at a pressure between 1 bar and 200 bar, more particularly between 40 bar and 150 bar. In one embodiment, the carbonation step is carried out at a temperature comprised between 30° C. to 150° C., more particularly between 70° C. and 150° C. In another embodiment, the reaction is performed in bulk.

In a particular embodiment, the carbonation step is conducted in the presence of gaseous or supercritical $CO_2$, at a pressure comprised between 40 and 150 bar, for example 50 bar, and at a temperature comprised between 70° C. and 90° C., for example 80° C. or comprised between 120° C. and 150° C., for example 135° C. In another embodiment, the carbonation step is conducted in the presence of gaseous or supercritical $CO_2$, at a pressure comprised between 40 and 150 bar, for example 60 bar, at a temperature comprised between 130° C. and 150° C., for example 140° C.

In one embodiment, the compound of formula (II) as defined above is prepared by epoxidation of the compound having the following formula (III):

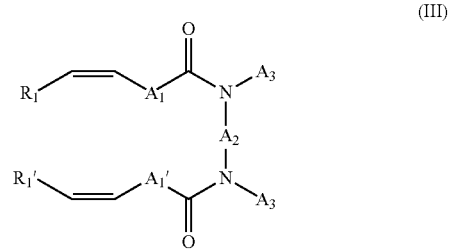

wherein $A_1$, $A_1'$, $A_2$, $A_3$, $R_1$ and $R_1'$ are defined above.

The epoxidation may be conducted in the presence of a peracid such as metachloroperbenzoic acid (m-CPBA), optionally in the presence of chloroform as a solvent.

In another embodiment, the compound of formula (III) as defined above is prepared by amidation of compounds having formulae (IV) and (IV'):

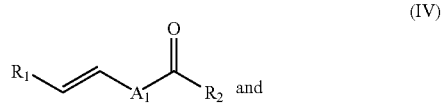

-continued (IV')

$$R_1' \overset{}{\underset{A_1'}{\diagdown}} \overset{O}{\underset{R_2}{\diagup}}$$

with a diamine having the following formula (V):

(V)

$$A_3 \overset{H}{\underset{N}{\diagdown}} A_2 \overset{H}{\underset{N}{\diagdown}} A_3$$

$R_1$, $R_1'$, $A_1$, $A_1'$, $A_2$ and $A_3$ being such as defined above, $R_2$ representing a halogen atom or a radical $OR_3$ with $R_3$ being a linear or branched alkyl group comprising from 1 to 10 carbon atom(s).

In a particular embodiment, $R_2$ is $OR_3$ with $R_3$ being a linear alkyl comprising from 1 to 5 carbon atom(s), preferably 1 carbon atom, or an halogen atom, preferably Cl. In a particular embodiment, the compounds of formulae (IV) and (IV') are chosen among: 1,4-diaminobutane, piperazine, N,N'-dimethyl-1,3-propanediamine and N,N'-dihexyl-1,10-decanediamine.

The invention also relates to the intermediate compound having the formula (II):

(II)

wherein $A_1$, $A_1'$, $A_2$, $A_3$, $R_1$ and $R_1'$ are as defined above.

Uses of the Biscarbonates of Formula (I)

The present invention also relates to the use of a compound of formula (I) as defined above, for the preparation of poly(hydroxyurethane)s and polycarbonates.

Polycarbonates are prepared with compounds of formula (I), in the presence of a base as catalyst, by ring opening polymerization in bulk or in solvent at temperature from 50° C. to 150° C.

The present invention also relates to a polymer susceptible to be obtained by the polymerisation of a compound of formula (I) as defined above and of at least one polyamine. In one embodiment, the polyamine is a diamine having the following formula (VI):

(VI)

$$H_2N \overset{B}{\diagdown} NH_2$$

wherein B is chosen from the group consisting of:
a linear or branched alkylene comprising from 1 to 200 carbon atom(s), one or more carbon atom(s) being optionally replaced by an oxygen atom;
an arylene radical comprising from 6 to 14 carbon atoms, optionally functionalized in ortho, meta or para with a linear or branched alkylene comprising from 1 to 10 carbon atom(s), one or more carbon atom(s) being optionally replaced by an oxygen atom;
a radical of formula —$B_1$—$B_2$— wherein:
$B_1$ is a cycloalkylene comprising from 3 to 15 carbon atoms, in which one or more carbon atom(s) is optionally substituted by at least one linear or branched alkyl group comprising from 1 to 15 carbon atom(s), and
$B_2$ is a linear or branched alkylene radical comprising from 1 to 15 carbon atom(s).

In one embodiment, B is chosen from the group consisting of:
a branched alkylene comprising from 1 to 200 carbon atom(s), preferably from 1 to 30 carbon atom(s), one or more carbon atom(s) being optionally replaced by an oxygen atom;
an arylene radical comprising 6 carbon atoms, optionally functionalized in ortho, meta or para with a linear alkylene comprising from 1 to 10 carbon atom(s), one or more carbon atom(s) being optionally replaced by an oxygen atom; and
a radical of formula —$B_1$—$B_2$— wherein:
$B_1$ is a cycloalkylene comprising 6 carbon atoms, in which one or more carbon atom(s) is optionally substituted by at least one linear alkyl group comprising from 1 to 15 carbon atom(s), and
$B_2$ is a linear alkylene radical comprising from 1 to 15 carbon atom(s).

More particularly, the diamine of formula (VI) as defined above is chosen from the group consisting of:
1,4-diaminobutane (4DA):

$$H_2N \diagdown \diagup \diagdown \diagup NH_2$$

isophorone diamine (IPDA):

Priamine® 1075 from CRODA;
the diamines derived from dimerized fatty acids, such as diacids Empol® (from BASF) or Unidyme® (from Arizona Chemical); and
Jeffamine:

with x or y+z being comprised between 2.5 and 68.

The different diamines may be used to introduce flexibility in the PHUs, by increasing the free volume between the polymer chains.

According to an embodiment, the polymer of the invention consists of n repetitive units having the following formula (U):

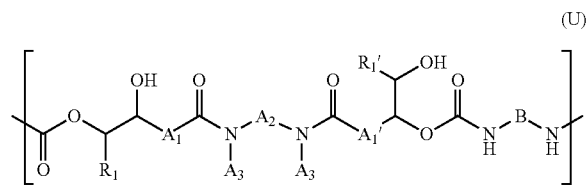

wherein $A_1$, $A_1'$, $A_2$, $A_3$, $R_1$, $R_1'$ and B are defined above.

More particularly, said polymer consists of n repetitive units having the formula (U), n being comprised between 2 and 200.

The present invention thus also relates to the polymer as defined above, especially the polymer having n repetitive units.

Said obtained polymers are poly(hydroxyurethane)s, more particularly, non isocyanate thermoplastic PHUs with high molar masses. An advantage of said obtained polymers is that their thermo-mechanical properties, such as the melting point and the glass transition temperature, can be controlled by the choice of the central block $A_2$ and $A_3$ as well as the $R_1$ and $R_1'$ radicals of said biscarbonates.

The present invention also relates to a method for preparing a poly(hydroxyurethane), comprising a step of polymerisation of a compound of formula (I) as defined above, and of at least one polyamine, said step being carried out at a temperature comprised between 60° C. and 150° C., optionally in the presence of a catalyst such as a strong base and/or a nucleophile.

The strong base may be chosen among Schreiner thiourea catalyst, alone or in combination with tertiary amines, the guanidine MTBD (7-methyl-1.5.7-triazabicyclo-[4.4.0]dec-5-ene), the amidine base DBU (1,8-diazabicyclo[5.4.0]un-dec-7-ene) and the guanidine TBD (1.5.7-triazabicyclo-[4.4.0]dec-5-ene). The nucleophile catalyst may be chosen among the 4-dimethylaminopyridine (DMPA), the salt LiCl and zinc acetate (ZnAc).

A co-catalyst may be added.

The invention also relates to the use of a compound of formula (II) as defined above for the preparation of epoxy resins. Epoxy resins may be prepared from a compound of formula (II) by homopolymerisation or copolymerisation with polyfunctional curatives or hardeners. Among the hardeners for epoxy resins, one may cite amines, acids, acid anhydrides, phenols, alcohols and thiols.

EXAMPLES

Experimental Methods

I. Preparation of the Biscarbonates of Formula (I)

Example 1: Preparation of the Compound UndBdA-b5CC Having the Formula

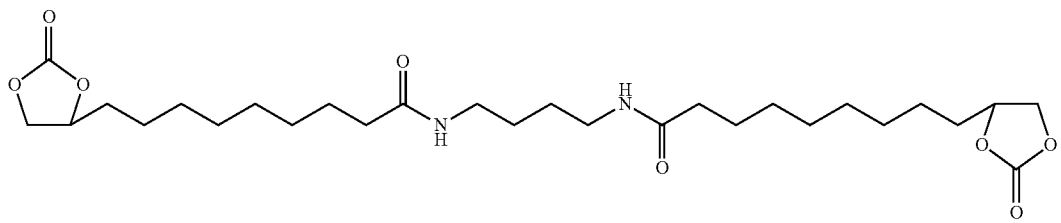 [SMILES: O=C(CCCCCCCCC1COC(=O)O1)NCCCCNC(=O)CCCCCCCCC1COC(=O)O1]

1. Amidation Reaction—Preparation of a Compound of Formula (III):

Methyl-undecenoate (UndME) (20 g, 101 mmol), 1,4-diaminobutane (4.4 g, 50 mmol) and TBD (702 mg, 5 mmol) (1:0.5:0.05) were stirred under nitrogen flow at 120° C. (4 h) then at 160° C. (2 h). The reaction flask was cooled down at 90° C. and NMP (60 mL) was added to end up with a homogeneous phase. The diamide UndBdA was slowly precipitated by reaching room temperature:

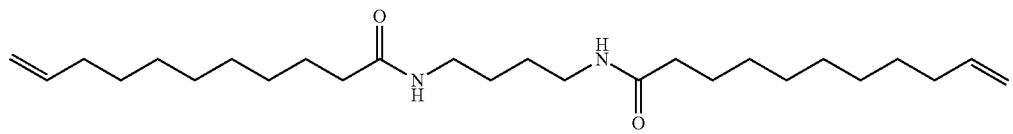 [SMILES: C=CCCCCCCCCC(=O)NCCCCNC(=O)CCCCCCCCC=C]

A filtration and washes with methanol were performed. Yield=83%.

UndBdA: $^1$H NMR (CDCl$_3$, 50° C., 400 MHz) δ (ppm): 5.79 (m, 2H), 4.98 (m, 4H), 3.26 (m, 4H), 2.15 (t, 4H), 1.99 (m, 4H), 1.65 (m, 4H), 1.53 (m, 4H), 1.40 (m, 4H), 1.32 (m, 16H). IR (cm$^{-1}$): 3295, 2918, 2847, 1630, 1537.

2. Epoxidation Reaction—Preparation of a Compound of Formula (II):

The diamide UndBdA and m-CPBA (3 eq. and 4.5 eq.) were stirred at room temperature in chloroform. After 1 day, the conversion of the double bonds, monitored by $^1$H NMR spectroscopy, were in the range 84% to 100%. The reaction mixture was then thoroughly washed with aqueous Na$_2$SO$_3$ (3×50 mL), aqueous NaHCO$_3$ (4×50 mL) and water (4×50 mL) until neutral pH. The organic layer was dried over anhydrous sodium sulfate filtered and solvent was remove on rotary evaporator to obtain the bUndBdA-bisEpoxide of formula:

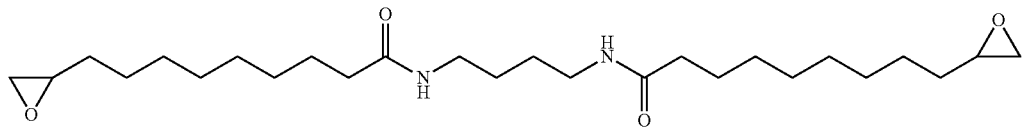 [SMILES: O=C(CCCCCCCCC1CO1)NCCCCNC(=O)CCCCCCCCC1CO1]

UndBdA-bisEpoxide: UndBdA (12.7 g, 30 mmol) and m-CPBA (23.4 g, 136 mmol, 4.5 eq.). The purity of UndBdA-bisEpoxide (80.4%) was determined by GC-FID. Yield=97%. $^1$H NMR (CDCl$_3$, 25° C., 400 MHz) δ (ppm): 5.79 (s, 2NH), 3.26 (m, 4H), 2.89 (m, 2H), 2.74 (t, 2H), 2.46 (m, 2H), 2.16 (t, 4H), 1.71 (m, 4H), 1.61-1.53 (m, 12H), 1.31 (m, 16H). IR (cm$^{-1}$): 3292, 2912, 2851, 1631, 1537.

3. Carbonation Reaction:

The bis-epoxide UndBdA-bisEpoxide was first pre-mixed with TBABr (3 wt %). Then the mixture was placed in a reactor and heated up at 140° C. Once the temperature got stabilized, carbon dioxide was slowly introduced into the reactor until 60 Bar. After 24 hours, the reactor was cooled down to room temperature and slowly depressurized to the atmospheric pressure. All the $^1$H NMR of all products revealed quantitative conversion by the disappearance of the protons of the epoxide.

UndBdA-b5CC: UndBdA-bisEpoxide (3 g, 6.6 mmol) and TBABr (0.09 g, 0.28 mmol, 4.5 wt %). Yield=95%.

$^1$H NMR (CDCl$_3$, 25° C., 400 MHz) δ (ppm): 5.83 (s, 2NH), 4.70 (m, 2H), 4.53 (t, 2H), 4.06 (t, 2H), 3.26 (m, 4H), 2.16 (t, 4H), 1.78 (m, 2H), 1.62 (m, 6H), 1.53 (m, 4H), 1.47 (m, 4H), 1.30 (m, 16H). $^{13}$C NMR (CDCl$_3$, 25° C., 100 MHz) δ (ppm): 173.81, 155.27, 77.22, 69.54, 39.20, 36.65, 33.94, 29.17, 26.91, 25.84, 24.43. IR (cm$^{-1}$): 3309, 2918, 2850, 1778, 1637, 1535.

Example 2: Preparation of the Compound UndPipdA-b5CC Having the Formula

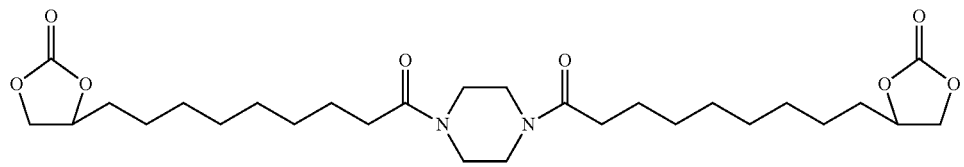

1. Amidation Reaction—Preparation of a Compound of Formula (III):

UndME, piperazine and TBD (1:0.5:0.05) were stirred in a round-bottom flask equipped with a bubbling system under inert atmosphere at 100° C. (2 h), then under nitrogen flow at 120° C. (4 h) and at 160° C. (2 h).

The diamide UndPipdA was purified by column chromatography and obtained as a yellow viscous liquid:

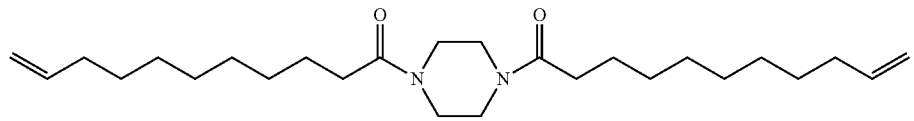 [SMILES: C=CCCCCCCCCC(=O)N1CCN(C(=O)CCCCCCCCC=C)CC1]

UndPipdA: UndME (20 g, 101 mmol), piperazine (4.3 g, 50 mmol) and TBD (702 mg, 5 mmol). UndPipdA was purified by column chromatography to eliminate completely the monoamide (eluent: cyclohexane/ethyl acetate with increasing percentage of ethyl acetate from 20% to 60%). Yield=68.2%.

$^1$H NMR (CDCl$_3$, 25° C., 400 MHz) δ (ppm): 5.79 (m, 2H), 4.94 (m, 4H), 3.62 (m, 4H), 3.44 (m, 4H), 2.32 (t, 4H), 2.03 (m, 4H), 1.63 (m, 4H), 1.35-1.29 (m, 20H). IR (cm$^{-1}$): 2918, 2847, 1650, 906.

2. Epoxidation Reaction—Preparation of a Compound of Formula (II):

The diamide and m-CPBA were stirred at room temperature in DCM (20 mL/g of product). After 1 day, the conversion of the double bonds, monitored by $^1$H NMR spectroscopy, were in the range 84% to 100%. The reaction mixture was then thoroughly washed with aqueous Na$_2$SO$_3$ (3×50 mL), aqueous NaHCO$_3$ (4×50 mL) and water (4×50 mL) until neutral pH. The organic layer was dried over anhydrous sodium sulfate filtered and solvent was remove on rotary evaporator to obtain the bis-epoxides UndPipdA-bisEpoxide having the formula:

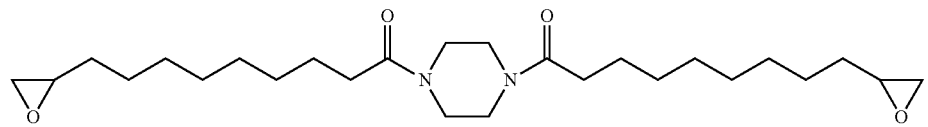 [SMILES: O=C(CCCCCCCCC1CO1)N1CCN(C(=O)CCCCCCCCC2CO2)CC1]

UndPipdA-bisEpoxide: UndPipdA (13.2 g, 31 mmol) and m-CPBA (16.3 g, 95 mmol, 3 eq.). The purity of UndPipdA-bisEpoxide (97.9%) was determined by GC-FID. Yield=84.5%.

$^1$H NMR (CDCl$_3$, 25° C., 400 MHz) δ (ppm): 3.61 (m, 4H), 3.45 (m, 4H), 2.88 (m, 2H), 2.73 (t, 2H), 2.45 (m, 2H), 2.32 (t, 4H), 1.61 (m, 4H), 1.49-1.44 (m, 8H), 1.34-1.30 (m, 16H). IR (cm$^{-1}$): 2913, 2848, 1651.

3. Carbonation Reaction:

The bis-epoxide UndPipdA-bisEpoxide was first pre-mixed with TBABr (3 wt %). Then the mixture was placed in a reactor and heated up at 135° C. Once the temperature got stabilized, carbon dioxide was slowly introduced into the reactor until 50 Bar. After 24 hours, the reactor was cooled down to room temperature and slowly depressurized to the atmospheric pressure. All the $^1$H NMR of all products revealed quantitative conversion by the disappearance of the protons of the epoxide.

UndPipdA-b5CC: UndPipdA-bisEpoxide (5 g, 11.1 mmol) and TBABr (0.15 g, 0.46 mmol, 3 wt %). Yield=98%.
$^1$H NMR (CDCl$_3$, 25° C., 400 MHz) δ (ppm): 4.69 (m, 2H), 4.51 (t, 2H), 4.06 (t, 2H), 3.62 (m, 4H), 3.45 (m, 4H), 2.32 (t, 4H), 1.76 (m, 2H), 1.70-1.63 (m, 8H), 1.47 (m, 2H), 1.31 (m, 16H). $^{13}$C NMR (CDCl$_3$, 25° C., 100 MHz) δ (ppm): 172.00, 155.15, 77.12, 69.47, 45.41 and 41.61, 33.93, 33.29, 29.25, 25.20, 24.42. IR (cm$^{-1}$): 2915, 2847, 1775, 1628.

Example 3: Preparation of the Compound UndPMedA-b5CC Having the Formula

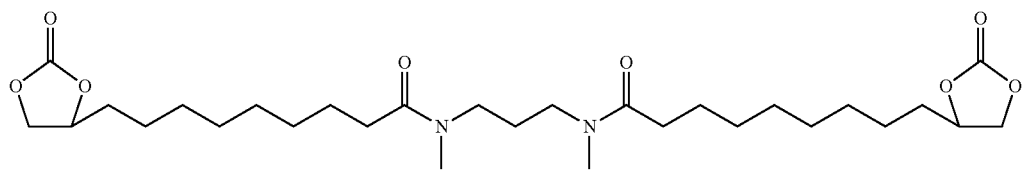 [SMILES: CN(CCCN(C)C(=O)CCCCCCCCC1COC(=O)O1)C(=O)CCCCCCCCC1COC(=O)O1]

1. Amidation Reaction—Preparation of a Compound of Formula (III):

UndME, N,N'-dimethyl-1,3-propanediamine and TBD (1:0.5:0.05) were stirred in a round-bottom flask equipped with a bubbling system under inert atmosphere at 100° C. (2 h), then under nitrogen flow at 120° C. (4 h) and at 160° C. (2 h). The diamide UndPMedA was purified by column chromatography and obtained as a yellow viscous liquid:

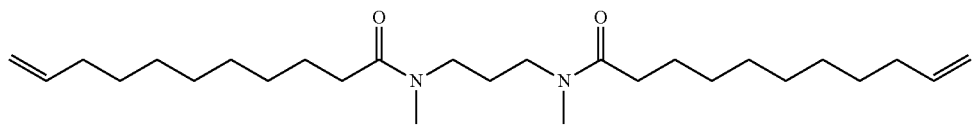 [SMILES: C=CCCCCCCCCC(=O)N(C)CCCN(C)C(=O)CCCCCCCCC=C]

UndPMedA: UndME (20 g, 101 mmol), N,N'-dimethyl-1,3-propanediamine (5.2 g, 50 mmol) and TBD (702 mg, 5 mmol). UndPMedA was purified by column chromatography to eliminate completely the monoamide (eluent: heptane/ethyl acetate with increasing percentage of ethyl acetate from 20% to 60%). Yield=79.3%.

$^1$H NMR (CDCl$_3$, 25° C., 400 MHz) δ (ppm): 5.80 (m, 2H), 4.95 (m, 4H), 3.35-3.25 (m, 4H), 2.98-2.89 (s, 6H), 2.26 (m, 4H), 2.01 (m, 4H), 1.75 (m, 2H), 1.59 (m, 4H), 1.34-1.28 (m, 20H). IR (cm$^{-1}$): 2924, 2850, 1639, 906.

2. Epoxidation Reaction—Preparation of a Compound of Formula (II):

The diamide UndPMedA and m-CPBA were stirred at room temperature in DCM (20 mL/g of product). After 1 day, the conversion of the double bonds, monitored by $^1$H NMR spectroscopy, were in the range 84% to 100%. The reaction mixture was then thoroughly washed with aqueous Na$_2$SO$_3$ (3×50 mL), aqueous NaHCO$_3$ (4×50 mL) and water (4×50 mL) until neutral pH. The organic layer was dried over anhydrous sodium sulfate filtered and solvent was remove on rotary evaporator to obtain the UndPMedA-bisEpoxide of formula:

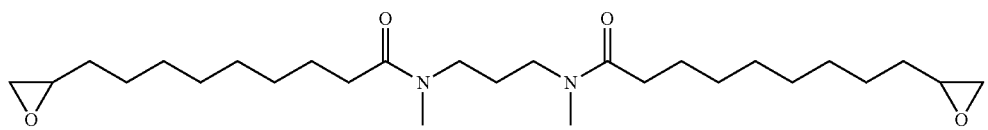 [SMILES: CN(CCCN(C)C(=O)CCCCCCCCC1CO1)C(=O)CCCCCCCCC1CO1]

UndPMedA-bisEpoxide: UndPMedA (20 g, 46 mmol) and m-CPBA (23.8 g, 138 mmol, 3 eq.). The purity of UndPMedA-bisEpoxide (93.9%) was determined by GC-FID. Yield=83.9%.

$^1$H NMR (CDCl$_3$, 25° C., 400 MHz) δ (ppm): 3.37 (m, 4H), 3.00-2.92 (s, 6H), 2.90 (m, 2H), 2.75 (t, 2H), 2.46 (m, 2H), 2.31 (m, 4H), 1.79 (m, 2H), 1.61 (m, 4H), 1.51 (m, 4H), 1.42 (m, 4H), 1.29 (m, 16H). IR (cm$^{-1}$): 2924, 2854, 1639.

3. Carbonation Reaction:

The bis-epoxide UndPMedA-bisEpoxide was first premixed with TBABr (3 wt %). Then the mixture was placed in a reactor and heated up at 80° C. Once the temperature got stabilized, carbon dioxide was slowly introduced into the reactor until 50 Bar. After 24 hours, the reactor was cooled down to room temperature and slowly depressurized to the atmospheric pressure. All the $^1$H NMR of all products revealed quantitative conversion by the disappearance of the protons of the epoxide.

UndPMedA-b5CC: UndPMedA-bisEpoxide (5 g, 10.7 mmol) and TBABr (0.15 g, 0.46 mmol, 3 wt %). The purity of UndPMedA-bisEpoxide (88.6%) was determined by GC-FID. Yield=96%.

$^1$H NMR (CDCl$_3$, 25° C., 400 MHz) δ (ppm): 4.69 (m, 2H), 4.51 (t, 2H), 4.05 (t, 2H), 3.34-3.27 (m, 4H), 2.98-2.89 (s, 6H), 2.27 (m, 4H), 1.79 (m, 6H), 1.61 (m, 6H), 1.47 (m, 2H), 1.30 (m, 16H). $^{13}$C NMR (CDCl$_3$, 25° C., 100 MHz) δ (ppm): 173.12, 155.20, 77.16, 69.51, 47.76-45.50, 35.51-33.08, 33.92, 33.65-33.38, 29.52-24.46, 26.53. IR (cm$^{-1}$): 2913, 2847, 1787, 1631.

Example 4: Preparation of the Compound UndDHexdA-b5CC Having the Formula

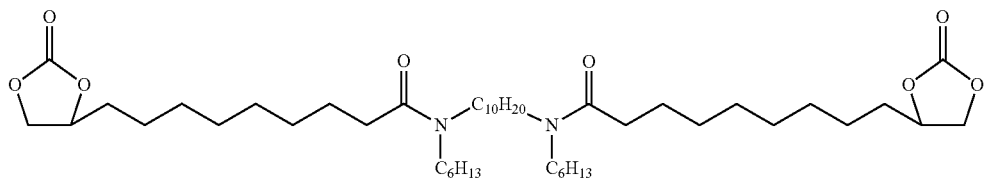

1. Amidation Reaction—Preparation of a Compound of Formula (III):

Concerning the preparation of UndDHexdA, the diamine (SebHex-diamine or N,N'-dihexyl-1,10-decanediamine) used as central block was synthesized in a first step, and then the amidation was performed. The SebHex-diamine was obtained by the reduction of the corresponding diamide issued from sebacoyl chloride and hexylamine. Hexylamine (9 g, 86.4 mmol, 2.05 eq.), triethylamine (20.7 mL, 143.3 mmol, 3.41 eq.), then chloroform (125 mL) were introduced in a round-bottom flash. Afterwards, the sebacoyl chloride (10 g, 42 mmol, 1 eq.) was added dropwise. The formation of a white precipitate due to the generation of triethylamine hydrochloride salt revealed the progress of the reaction. After filtration and washes with hot water, the organic phase was dried over anhydrous sodium sulfate, filtered and the chloroform was removed on rotary evaporator. After drying, the diamide was reduced by $LiAlH_4$ (3 eq. per function) in dried THF under reflux overnight. Then, an aqueous solution of potassium sodium tartrate at 1 mol·L−1 (200 mL) was added to the reaction mixture placed into an ice bath. The SebHex-diamine was recovered after filtration followed by extraction of the filtrate with ethyl acetate. SebHex-diamine was purified by column chromatography (eluent: ethyl ether/methanol with increasing percentage of methanol from 0% to 31%). Yield=84.6%.

SebHexdiamine:

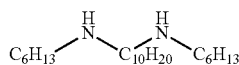

SebHex-diamine: $^1H$ NMR ($CDCl_3$, 25° C., 400 MHz) δ (ppm): 2.57 (1, 8H), 1.46 (m, 8H), 1.27 (m, 24H), 0.81 (t, 6H).

To SebHex-diamine (8.4 g, 25 mmol), dried THF (100 mL) and triethylamine (5.5 g, 55 mmol, 1.1 eq.) were added. Then undecenyl chloride (10 g, 49 mmol) was added dropwise. The reaction mixture was then stirred at room temperature for 2 hours. UndDHexdA was purified by filtration of the formed salt, followed by column chromatography to eliminate completely the monoamide (eluent: heptane/ethyl acetate (95/5)). Yield=91.3%.

The compound UndHexa is obtained:

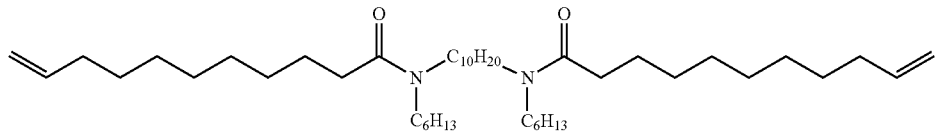

UndDHexdA: $^1H$ NMR ($CDCl_3$, 50° C., 400 MHz) δ (ppm): 5.80 (m, 2H), 4.94 (m, 4H), 3.27 (m, 4H), 3.19 (m, 4H), 2.27 (t, 4H), 2.02 (m, 4H), 1.62 (m, 4H), 1.51 (m, 8H), 1.36-1.28 (m, 40H), 0.88 (m, 6H). IR ($cm^{-1}$): 2924, 2851, 1642, 906.

2. Epoxidation Reaction—Preparation of a Compound of Formula (II):

The N,N'-dihexyl-1,10-decanediamine and m-CPBA (were stirred at room temperature in DCM (20 mL/g of product). After 1 day, the conversion of the double bonds, monitored by $^1H$ NMR spectroscopy, were in the range 84% to 100%. The reaction mixture was then thoroughly washed with aqueous $Na_2SO_3$ (3×50 mL), aqueous $NaHCO_3$ (4×50 mL) and water (4×50 mL) until neutral pH. The organic layer was dried over anhydrous sodium sulfate filtered and solvent was remove on rotary evaporator to obtain the UndDHexdA-bisEpoxide having the formula:

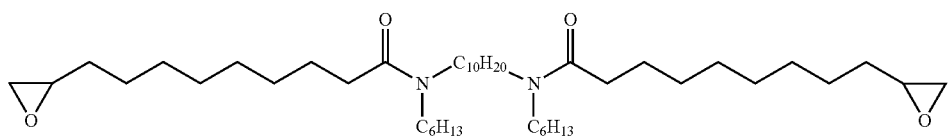

UndDHexdA-bisEpoxide: UndDHexdA (10 g, 15 mmol) and m-CPBA (7.7 g, 44 mmol, 3 eq.). Yield=54.4%. $^1H$ NMR ($CDCl_3$, 25° C., 400 MHz) δ (ppm): 3.28 (m, 4H), 3.19 (m, 4H), 2.89 (m, 2H), 2.73 (t, 2H), 2.46 (m, 2H), 2.27 (t, 4H), 1.62 (m, 4H), 1.43 (m, 16H), 1.31 (m, 40H), 0.88 (m, 6H). IR ($cm^{-1}$): 2924, 2853, 1637.

3. Carbonation Step:

The bis-epoxide UndDHexdA-bisEpoxide was first pre-mixed with TBABr (3 wt %). Then the mixture was placed in a reactor and heated up at 80° C. Once the temperature got stabilized, carbon dioxide was slowly introduced into the reactor until 50 Bar. After 24 hours, the reactor was cooled down to room temperature and slowly depressurized to the atmospheric pressure. All the $^1H$ NMR of all products revealed quantitative conversion by the disappearance of the protons of the epoxide.

UndDHexdA-b5CC: UndDHexdA-bisEpoxide (3 g, 4.2 mmol) and TBABr (0.09 g, 0.28 mmol, 3 wt %). Yield=88.7%.

$^1H$ NMR ($CDCl_3$, 25° C., 400 MHz) δ (ppm): 4.67 (m, 2H), 4.50 (t, 2H), 4.04 (t, 2H), 3.25 (m, 4H), 3.17 (m, 4H), 2.24 (t, 4H), 1.75 (m, 2H), 1.65-1.60 (m, 6H), 1.45 (m, 12H), 1.29 (m, 40H), 0.87 (m, 6H). $^{13}C$ NMR ($CDCl_3$, 25° C., 100 MHz) δ (ppm): 173.10, 155.14, 76.97, 69.27, 47.73-45.56, 33.59, 32.77, 31.27-22.30, 13.78. IR ($cm^{-1}$): 2924, 2854, 1795, 1634.

II. Polymers Synthesis and Characterizations

General Procedure for poly(hydroxyurethane)s

The bis 5-membered cyclic carbonates (UndBdA-b5CC, UndPipdA-b5CC, UndPMedA-b5CC and UndDHexdA-b5CC) and the diamines (1,4-diaminobutane (4DA), isophorone diamine (IPDA), Jeffamine 400 g·mol$^{-1}$, CRODA diamine (Priamine 1075®) were weighted in a test tube. The polymerization reactions were conducted in bulk under static nitrogen. The mixture was stirred at the selected temperature: 140° C. (for UndBdA-b5CC and UndPipdA-b5CC), 120° C. (for UndPMedA-b5CC and UndDHexdA-b5CC). No catalysts were added for the polymerization reactions. The obtained PHUs were brown to yellow and viscous to solid in nature. SEC data, which are exposed in Table 1, indicate the formation of PHUs with molar masses in the range 11 000 to 31 000 g·mol$^{-1}$ after one to 12 days in bulk at the polymerization temperature (70° C. to 140° C.).

TABLE 1

Molar masses and dispersities of the PHUs from 5-membered cyclic carbonates according to the invention.

| Sample | Used b5CC | Diamine | Temperature (° C.) | Time | Conversion (%)[1] | Mn (g·mol$^{-1}$)[2] | Dispersity |
|---|---|---|---|---|---|---|---|
| PHU-BdA-1 | UndBdA-b5CC | IPDA | 140 | 5h | 64.1 | 15 300 | 1.3 |
|  |  |  |  | 13d | 97.6 | 18 900 | 2.4 |
| PHU-BdA-2 | UndBdA-b5CC | CRODA (Priamine 1075®) | 140 | 5h | 97.6 | 14 900 | 1.5 |
| PHU-BdA-3 | UndBdA-b5CC | Jeffamine | 140 | 5h | 84.3 | 14 600 | 1.3 |
|  |  |  |  | 6d | 98.9 | 20 900 | 2.6 |
| PHU-PipdA-1 | UndPipdA-b5CC | IPDA | 140 | 5h | 76.3 | 16 500 | 1.5 |
|  |  |  |  | 1d | 87.0 | 18 200 | 1.5 |
| PHU-PipdA-2 | UndPipdA-b5CC | CRODA | 140 | 5h | 91.9 | 19 300 | 1.7 |
|  |  |  |  | 1d | 93.2 | 19 200 | 1.7 |
| PHU-PipdA-3 | UndPipdA-b5CC | Jeffamine | 140 | 5h | 46.7 | 11 200 | 1.2 |
|  |  |  |  | 3d | 91.5 | 23 300 | 2.9 |
| PHU-PMedA-1 | UndPMedA-b5CC | IPDA | 120 | 5h | 53.5 | 11 000 | 1.2 |
|  |  |  |  | 12d | 91.5 | 31 100 | 2.2 |
| PHU-PMedA-2 | UndPMedA-b5CC | CRODA | 120 | 5h | 87.6 | mm[3] | mm[3] |
|  |  |  |  | 6d | 94.4 | 28 700 | 1.7 |
| PHU-PMedA-3 | UndPMedA-b5CC | Jeffamine | 120 | 5h | 12.4 | mm[3] | mm[3] |
|  |  |  |  | 6d | 84.1 | 20 700 | 1.4 |
| PHU-DHexdA-1 | UndDHexdA-b5CC | IPDA | 120 | 1d | ns | ns | ns |
| PHU-DHexdA-2 | UndDHexdA-b5CC | CRODA | 120 | 1d | nd | nd | nd |
| PHU-DHexdA-3 | UndDHexdA-b5CC | Jeffamine | 120 | 1d | nd | nd | nd |
| PHU-DHexdA-4 | UndDHexdA-b5CC | 4DA | 120 | 1d | nd | nd | nd |

[1]Calculated by FTIR-ATR using the equation:

$$\chi = 100 - \frac{(H_{cc}/H_{Ad})_t}{(H_{cc}/H_{Ad})_{t=0}} \times 100$$

where x, t, HCC and HAd are the conversion, the time, the height of the peaks corresponding to the cyclic carbonate and amide carbonyls respectively. [2]SEC in DMF with 1 wt % LiBr—calibration PS standards. The analyses were performed on the soluble fraction. The given data correspond to the main peak in SEC. The results presented here are for the fraction at 5 h and for the best molar masses fraction or the last soluble fraction observed for each sample. [3]Highly multi modal molar masses.

III. Thermo-Mechanical Properties of the Prepared Poly(Hydroxyurethane)s

The thermo-mechanical properties of the synthesized PHUs are correlated with their chemical structure. Table 2 summarizes the glass transition and melting temperatures of the PHUs.

TABLE 2

Thermo-mechanical properties of the synthetisized PHUs.

| Sample | Time d (day) | $T_g$ (° C.)[1] | Tm (° C.)[1] |
|---|---|---|---|
| PHU-BdA-1 | 13 d | 40 | 115[2] |
| PHU-BdA-2 | 6 d | 2 | 115 |
| PHU-BdA-3 | 6 d | −21 | 109 |
| PHU-PipdA-1 | 6 d | 55 | — |
| PHU-PipdA-2 | 1 d | −2 | — |

TABLE 2-continued

Thermo-mechanical properties of the synthetisized PHUs.

| Sample | Time d (day) | $T_g$ (° C.)[1] | Tm (° C.)[1] |
|---|---|---|---|
| PHU-PipdA-3 | 6 d | −15 | — |
| PHU-PMedA-1 | 6 d | 32 | — |
| PHU-PMedA-2 | 1 d | −4 | — |
| PHU-PMedA-3 | 6 d | −17 | — |
| PHU-DHexdA-1 | 6 d | 3 | — |
| PHU-DHexdA-2 | 1 d | −18 | — |
| PHU-DHexdA-3 | 6 d | −29 | — |
| PHU-DHexdA-4 | 1 d | −13 | — |

[1]Determined by DSC at 10° C. min$^{-1}$
[2]With crystallization upon heating

Amorphous PHUs were obtained with UndPipdA-b5CC, UndPMedA-b5CC and UndDHexdA-b5CC. With UndBdA-b5CC as comonomer, the PHUs obtained were semi-crystalline in nature. The presence of hydrogen bonds from the amide linkages of UndBdA-b5CC favored interactions between polymer chains and thus the crystallization of the resulting PHUs.

The structure of the $A_2$ group in the synthetized PHUs affects the glass transition temperature of the PHUs:
  the cyclic structure of $A_2$ together with $A_3$ and the two nitrogen atoms bearing them in UndPipdA-b5CC led to higher glass transition temperature,
  the longer the $A_3$ group is, the lower the glass transition is when comparing UndPMedA-b5CC and UndDHexdA-b5CC.

Moreover, the use of a cyclic aliphatic amine induced the formation of a PHU with a glass transition temperature of 39.9° C. However, while using CRODA diamine, a lower glass transition temperature (2.4° C.) was obtained. Indeed, the resulting B group in the polymer backbone, due to it chemical structure, plasticize the final so-formed PHU.

The PHU-BdA-3 with Jeffamine (400 g·mol-1) as comonomer reached an even lower glass transition of –21° C., which can be explained by the polyether structure of the Jeffamine.

Lastly, the PU-dA-1, synthesized by the classical alcohol/isocyanate route exhibiting similar molecular structure (alcohol obtained from mercaptoethanol addition on the diene of formula (III), and isocyanate obtained from phosgene addition on the diamine), demonstrated a glass transition temperature and a melting point of 47° C. and 117° C. respectively. In the case of PHU-BdA-1, synthesized by the cyclic carbonate/amine route, the glass transition temperature and melting point are 40° C. and 115° C., as shown in Table 3 below.

TABLE 3

Comparison between PUs and PHUs.

| Sample | Route | Mn (g · mol⁻¹)[1] | Dispersity | Tg (° C.)[2] | Tm (° C.)[2] |
|---|---|---|---|---|---|
| PU-dA-1 | alcohol/isocyanate | ns | ns | 47 | 117 |
| PHU-BdA-1 | cyclic carbonate/amine | 18 922 | 2.4 | 40 | 115[3] |

[1]SEC-Size Exclusion Chromatography-in DMF with 1 wt % LiBr-calibration PS standards.
[2]Determined by DSC at 10° C. min⁻¹
[3] With crystallization upon heating Therefore, the obtained PHUs according to the invention are similar to PUs prepared by the toxic alcohol/isocyanate way.

Material

Methyl 10-undecenoate (>96.0%) and butane-1,4-diamine (4DA, 99%) were supplied by TCI, Europe.

1,5,7-triazabicyclo[4.4.0]dec-5-ene (TBD, 98%), N,N-dimethylformamide (DMF, anhydrous grade), N-Methyl-2-pyrrolidone (NMP), lithium aluminum hydride (LiAlH$_4$) (95%), sodium hydrate (NaH) (60% dispersion in mineral oil), 10-undecenoyl chloride (97%), 3-chloroperbenzoic acid (77%), hexylamine (99%), tetrabutylammonium bromide (TBABr, >98%), poly(propylene glycol) bis(2-aminopropyl ether) (Jeffamine, $\overline{M}_n$=400 g·mol⁻¹) were obtained from Sigma-Aldrich.

Piperazine (Pip, anhydrous, 99%), N,N'-dimethylpropane-1,3-diamine (PMe, 97%), and sebacoyl chloride (97%) were purchased from Alfa Aesar.

Isophorone diamine (IPDA, >99%) was obtained from Fisher. The dimer fatty acid-based diamine (Priamine 1075) was purchased from CRODA.

All products and solvents (reagent grade) were used as received except otherwise mentioned. The solvents were of reagent grade quality and were purified wherever necessary according to the methods reported in the literature.

What is claimed is:
1. A compound of formula (I):

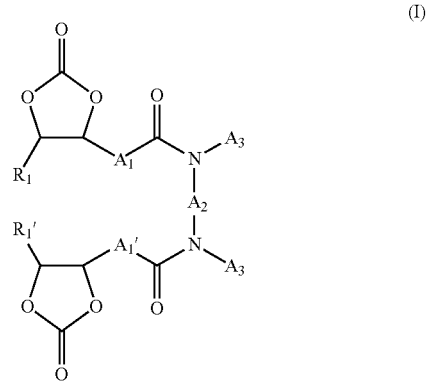

wherein:
  $A_1$ and $A_1'$ are independently from each other a linear or branched alkylene radical comprising from 1 to 20 carbon atom(s);
  $A_2$ is chosen from the group consisting of:
  a linear or branched alkylene radical comprising from 1 to 200 carbon atom(s), one or more carbon atom(s) being optionally replaced by an oxygen atom;
  an arylene radical comprising from 6 to 14 carbon atoms, optionally functionalized in ortho, meta or para, with a linear or branched alkyl radical comprising from 1 to 10 carbon atom(s), one or more carbon atom(s) being optionally replaced by an oxygen atom;
  a radical of formula -$B_1$-$B_2$- wherein:
  $B_1$ is a cycloalkylene comprising from 3 to 15 carbon atoms, in which one or more carbon atom(s) is optionally substituted by at least one linear or branched alkyl group comprising from 1 to 15 carbon atom(s), and
  $B_2$ is a linear or branched alkylene radical comprising from 1 to 15 carbon atom(s);
  $A_3$ is H or a linear or branched alkyl radical comprising from 1 to 15 carbon atom(s);
  or wherein $A_2$ and $A_3$, together with the two nitrogen atoms bearing them, may form a saturated heterocyclyl group comprising from 3 to 8 members; and
  $R_1$ and $R_1'$ are independently from each other H or a linear or branched alkyl radical comprising from 1 to 20 carbon atom(s).

2. The compound of formula (I) according to claim 1, wherein $A_2$ is a linear or branched alkylene comprising from 1 to 10 carbon atom(s).

3. The compound of formula (I) according to claim 1, wherein $A_3$ is H or an alkyl radical comprising from 1 to 10 carbon atom(s).

4. The compound of formula (I) according to claim 1, wherein $A_2$ and $A_3$, together with the two nitrogen atoms bearing them, form a saturated heterocyclyl group comprising from 5 to 8 members.

5. The compound of formula (I) according to claim 1, wherein $R_1$ and $R_1'$ are H.

6. The compound of formula (I) according to claim 1, having one of the following formulae:

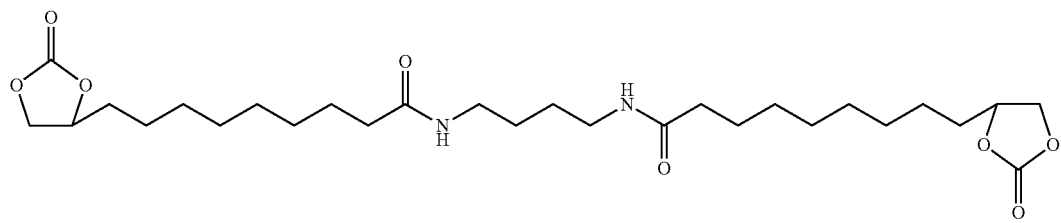

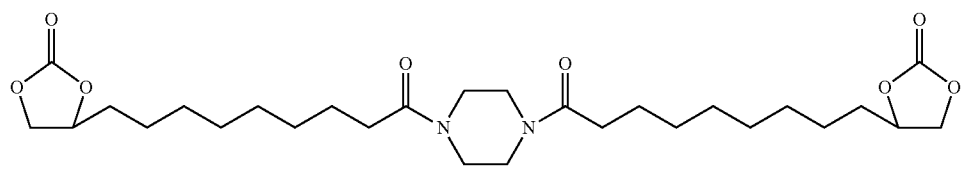

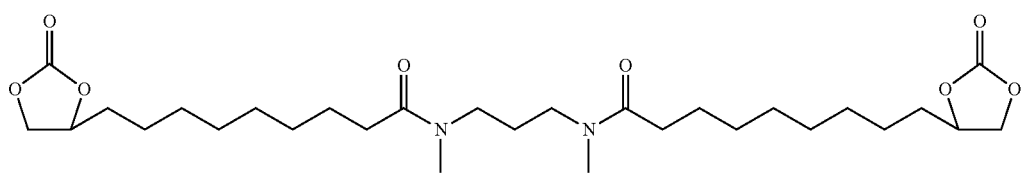

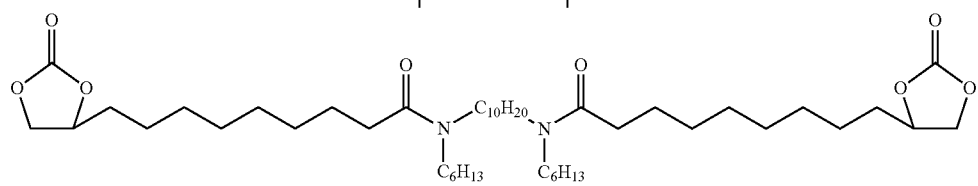

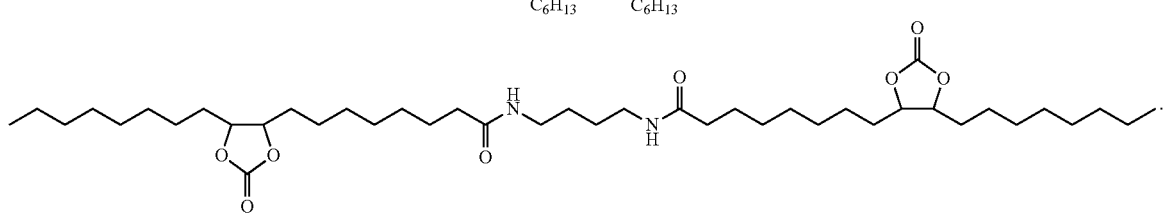

7. A method for preparing a compound of formula (I) according to claim 1, comprising a carbonation step of a compound having formula (II):

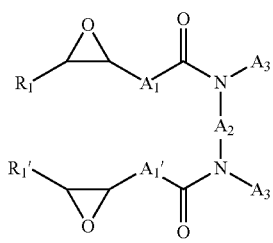
(II)

wherein $A_1, A_1', A_2, A_3, R_1$ and $R_1'$ are as defined in claim 1.

8. The method for preparing the compound of formula (I) according to claim 7, wherein the compound of formula (II) is prepared by epoxidation of the compound having the following formula (III)

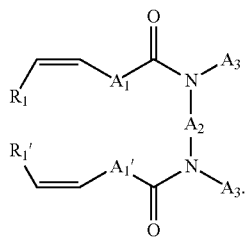
(III)

9. The method according to claim 7, wherein the compound of formula (III) is prepared by amidation of compounds having formulae (IV) and (IV'):

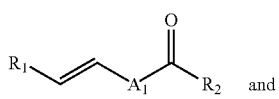
(IV)

and

-continued

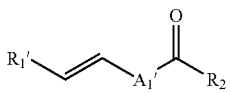
(IV')

with a diamine having the following formula (V):

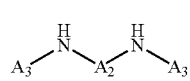
(V)

$R_1, R_1', A_1, A_1', A_2$ and $A_3$ being such as defined in claim 1, $R_2$ representing a halogen atom or a radical $OR_3$ with $R_3$ being a linear or branched alkyl group comprising from 1 to 10 carbon atom(s).

10. A polymer susceptible to be obtained by the polymerisation of a compound of formula (I) according to claim 1 and of at least one polyamine.

11. The polymer according to claim 10, wherein the polyamine is a diamine having the following formula (VI):

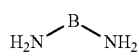
(VI)

wherein B is chosen from the group consisting of:
- a linear or branched alkylene comprising from 1 to 200 carbon atom(s), one or more carbon atom(s) being optionally replaced by an oxygen atom;
- an arylene radical comprising from 6 to 14 carbon atoms, optionally functionalized in ortho, meta or para with a linear or branched alkylene comprising from 1 to 10 carbon atom(s), one or more carbon atom(s) being optionally replaced by an oxygen atom; and
- a radical of formula —$B_1$—$B_2$- wherein:
  $B_1$ is a cycloalkylene comprising from 3 to 15 carbon atoms, in which one or more carbon atom(s) is optionally substituted by at least one linear or branched alkyl group comprising from 1 to 15 carbon atom(s), and
  $B_2$ is a linear or branched alkylene radical comprising from 1 to 15 carbon atom(s).

12. The polymer according to claim 11, said polymer consisting of n repetitive units having the following formula (U)

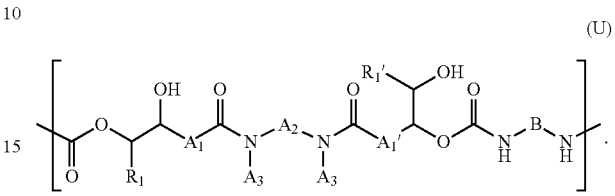
(U)

13. A method for preparing a poly(hydroxyurethane), comprising a step of polymerisation of a compound of formula (I) according to claim 1, and of at least one polyamine, said step being carried out at a temperature comprised between 60° C. and 150° C., optionally in the presence of a catalyst such as a strong base and/or a nucleophile.

14. An intermediate compound of formula (II):

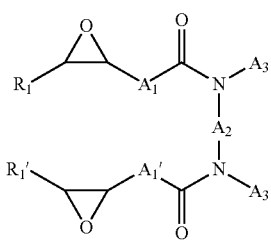
(II)

wherein $A_1, A_1', A_2, A_3, R_1$ and $R_1'$ are as defined in claim 1.

* * * * *